United States Patent [19]

Zinck et al.

[11] Patent Number: 5,427,233
[45] Date of Patent: Jun. 27, 1995

[54] CONDOM CARRYING TOKEN

[75] Inventors: Dorian K. Zinck, 521 Beech Rd., West Palm Beach, Fla. 33409; Wayne R. Zinck, Las Vegas, Nev.

[73] Assignee: Dorian K. Zinck, West Palm Beach, Fla.

[21] Appl. No.: 131,136

[22] Filed: Oct. 4, 1993

[51] Int. Cl.⁶ .................... B65D 85/14; A45C 11/00
[52] U.S. Cl. ........................ 206/69; 206/37; 206/38; 220/4.21
[58] Field of Search .............. 206/69, 37, 38, 38.1, 206/804; 220/4.21, 4.27; 224/163

[56] References Cited

U.S. PATENT DOCUMENTS

| | | | |
|---|---|---|---|
| D. 142,357 | 9/1945 | Younghusband | 206/38 R |
| D. 318,565 | 7/1991 | Kearney et al. | |
| D. 329,136 | 9/1992 | Sanchez | |
| 385,106 | 6/1888 | Fitch | 206/37 R |
| 1,265,324 | 5/1918 | Greene | 224/163 X |
| 1,995,428 | 3/1935 | Keely | 220/4.21 X |
| 2,125,620 | 8/1938 | Schlumbohm | 220/4.21 X |
| 2,326,414 | 8/1943 | Thompson | 220/4.27 |
| 2,621,782 | 12/1952 | Reifers | 220/4.21 X |
| 2,706,065 | 4/1955 | Stone | 220/4.21 X |
| 3,111,152 | 11/1963 | Goessling | 206/38.1 |
| 3,765,528 | 10/1973 | Parisot | 206/804 X |
| 4,738,357 | 4/1988 | Martin et al. | |
| 4,741,434 | 5/1988 | Liebman | |
| 4,765,501 | 8/1988 | Kao | 220/4.21 |
| 4,776,460 | 10/1988 | Hoffman | |
| 4,781,288 | 11/1988 | Wing | |
| 4,805,820 | 2/1989 | Kearney et al. | |
| 4,875,491 | 10/1989 | Parrone | |
| 4,892,188 | 1/1990 | Meadows | |
| 4,899,395 | 2/1990 | Spector | |
| 4,969,821 | 11/1990 | Smith | |
| 4,972,557 | 11/1990 | Williams | 224/163 X |
| 5,005,695 | 4/1991 | Tennefos et al. | |
| 5,007,756 | 4/1991 | Wey | |
| 5,117,841 | 6/1992 | McBeth | |
| 5,170,887 | 12/1992 | Potts et al. | |
| 5,172,430 | 12/1992 | Lerma-Solis | |

FOREIGN PATENT DOCUMENTS

WO92/20595  11/1992  WIPO .................... 206/69

OTHER PUBLICATIONS

"The FBI-KGB War" excerpt p. 270, 1986 Random House.

Primary Examiner—Bryon P. Gehman
Attorney, Agent, or Firm—John C. Smith

[57] ABSTRACT

A condom holding and concealment device for providing damage resistant storage for the condom as well as a discrete method of storage is provided by enclosing the condom in an outer shell made from commonly used items such as coins. In the preferred embodiment, the coins are hollowed out to allow a condom to be safely stored in a change purse or pocket. The attaching device may also be constructed such that it is waterproof to allow the coin to be carried in a bathing suit, etc.. Optional lifting springs or pull tabs may be used to more easily remove the condom from the package. Any item similar in shape to a coin, such as poker chips, casino chips, medallions, etc., may be used in place of a coin.

4 Claims, 13 Drawing Sheets

CONDOM CARRYING TOKEN

BACKGROUND OF THE INVENTION

1. Technical Field

The present invention relates to condoms. In particular, it relates to devices for carrying concealed condoms.

2. Background Art

Historically, condoms were used for a variety of purposes, including prevention of pregnancy and also the prevention of a number of sexually transmitted diseases. Typically, the task of obtaining condoms fell on the male partner for several reasons. For example, in times past, a male could purchase condoms without any social stigma while a woman, particularly an unmarried women, may have felt uncomfortable purchasing condoms due to the stigma associated with the appearance of unchastity. In addition, both men and women may feel uncomfortable carrying loose packages of condoms on their person for a variety of reasons. As a result, many men and women who did not carry packaged condoms have exposed themselves to both disease and unwanted pregnancy.

In addition to social obstacles to carrying condoms, condom packages are relatively fragile. Even if condoms are carried in a wallet or purse, they are often subject to damage due to the fragility of their packaging. In addition to impact damage, condom packages may also be damaged due to environmental conditions such as exposure to water, etc. As a result of these problems, even persons who carry condoms may be exposed to disease or pregnancy due to damage sustained to the condom package.

Unfortunately, the development of new, contagious and often lethal diseases such as HIV and AIDS has created a much greater need for caution in sexual relations. Since a principle method of avoiding AIDS is the wearing of condoms, a convenient manner of carrying condoms on one's person is desirable for both men and women. In particular, a device for discretely carrying condoms would be advantageous in encouraging condom use by increasing the possibility that they are available.

Some attempts have been made to increase the variety of packaging devices used for condoms. For example, a variety of containers have been developed to protect condom packages from damage. Typical examples of this approach are hardened containers which provide impact protection to condom packages, but do not effectively conceal the condom due to the shape of the container. While these provide a solution to impact damage, they do not encourage use both because they are not discrete, and also because they require the user to remember to take the condom case with them. Depending to where the user is going, this may be inconvenient and discourage use.

Attempts to conceal condoms have been made principally in the area of hidden pockets in garments. It is well known in the art not only to design garments with hidden pockets, but also to attach pockets to undergarments with adhesives, etc., for the purpose of carrying condoms out of sight. Of course, when condoms are kept in undergarment pockets, they typically are not in protective containers for comfort reasons. Other attempts to conceal condoms, such as in one known method of placing condoms in ball point pens, has not solved the problem of convenience, since the pen must be carried much like the hardened cases discussed above, and in addition, is subject to water damage. Likewise, items such as key chains when used as condom holders may not enhance the users goal of discretion and privacy.

Another problem associated with prior art condom packaging is ease of use. As packaging devices become more elaborate to solve one problem or another, they become more difficult to use. This is a particular problem with condoms since the users are often in a hurry as well as in the dark.

While addressing various problems related to condom use, the prior art has failed to provide condom packages with the combination of features which would encourage greater availability and the subsequent greater protection in the face of mounting health hazards. In particular, the prior art has not provided a packaging scheme which is easy to use, incorporates both physical protection for the condom from impact and environmental damage, is convenient to carry in normal use and in outdoor activities such as swimming, and that is protective of the user's privacy by incorporating camouflage to allow the package to go unnoticed even when seen. This last feature would be especially valuable to encourage members of both sexes to carry condoms for their protection.

SUMMARY OF THE INVENTION

The improvements inherent in the invention disclosed herein are accomplished by enclosing the condom in an outer shell made from commonly used items such as coins. In the preferred embodiment, the coins are sliced in half, hollowed out, and provided with an attaching device such as threading, cam locks, etc. to allow a condom to be safely stored in a change purse or pocket. The attaching device may also be constructed such that it is waterproof to allow the coin to be carried in a bathing suit, etc. Optional lifting springs or pull tabs may be used to more easily remove the condom from the package. Any item similar in shape to a coin, such as poker chips, casino chips, medallions, etc., may be used in place of a coin.

DESCRIPTION OF THE PREFERRED EMBODIMENT

For ease of discussion, the following terms will be used in this disclosure. The term "token" will be used to describe any coin shaped object used for the condom holder. The token may in fact be a real coin, such as a silver dollar, a medallion, a souvenir coin, a poker chip, a casino chip, etc. The only requirements are that the token must be of a size suitable to hold a condom, and must be made of material suitable for the particular embodiments discussed below.

Figure 1:
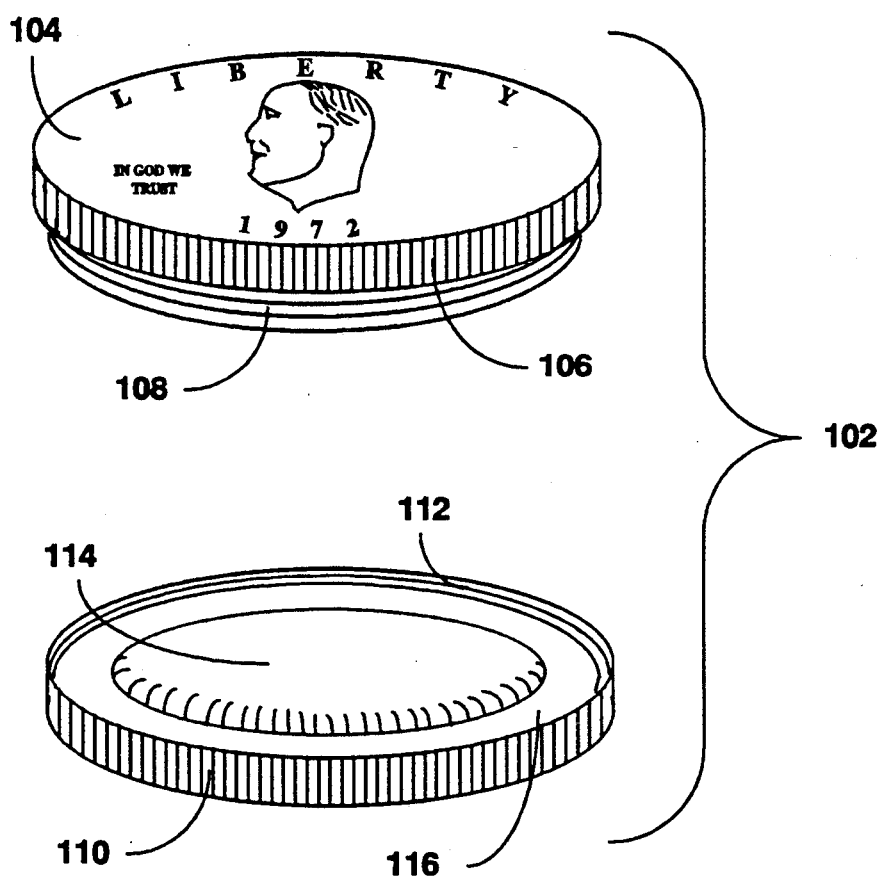
FIG. 1 is a diagram showing the token as a hollowed out, threaded coin.

Referring to FIG. 1, a token 102 is shown constructed from a coin. Token 102 is split in two as shown and the interior portion of the metal is removed. The remaining metal in the upper portion of token 102 forms a first side 104 and a first edge 106. Thread 108 may be machined from the metal in token 102. However, those skilled in the art will recognize that thread 108 can easily be constructed as a separate unit and attached to first side 104 and/or first edge 106 by conventional means, such as welding.

The lower half of token 102 is similar in construction, second side 116 is formed from a side of token 102 as well as second edge 110. Thread 112 may likewise be machined from token 102 or manufactured separately and attached by conventional means. Condom 114, wrapped in a conventional strength condom covering, is shown only for illustrative purposes and is not part of token 102. However, to best take advantage of the limited available space, condom 114 should have a wrapper which is generally circular and should be sealed such that it does not extend excessively past the edge of condom 114. Likewise, the wrapper should be watertight to ensure that any lubricants, spermicides, etc. do not leak. Sealed wrapping techniques are well known in the art. An additional space saving benefit may be obtained by not rolling the condom 114 as is typically done. If condom 114 is packaged flat, in a wrapper designed to fit the inside of token 102, there will be no wasted space in the storage area of token 102 resulting in additional space available for additional condoms.

The height of threads 108, 112 is not critical. In the preferred embodiment, threads 108, 112 are of a size suitable to allow first edge 106 and second edge 110 to contact when the upper and lower portions of token 102 are screwed together by threads 108, 112, and also to allow firm attachment of the upper and lower portions of token 102.

Threads 108, 112 may also optionally be covered, or coated, with material suitable for creating a watertight seal or manufactured from a flexible waterproof material, such as plastic. Materials used for this purpose are well known in the art. By sealing threads 108, 112 to the upper and lower portions of token 102, a watertight seal is provided to further protect the condom 114. This type of sealing is well known in the art. The watertight seal will allow condom 114 to be carried where it would not ordinarily be able to go without damage, such as in the pocket of a bathing suit.

Figure 2:
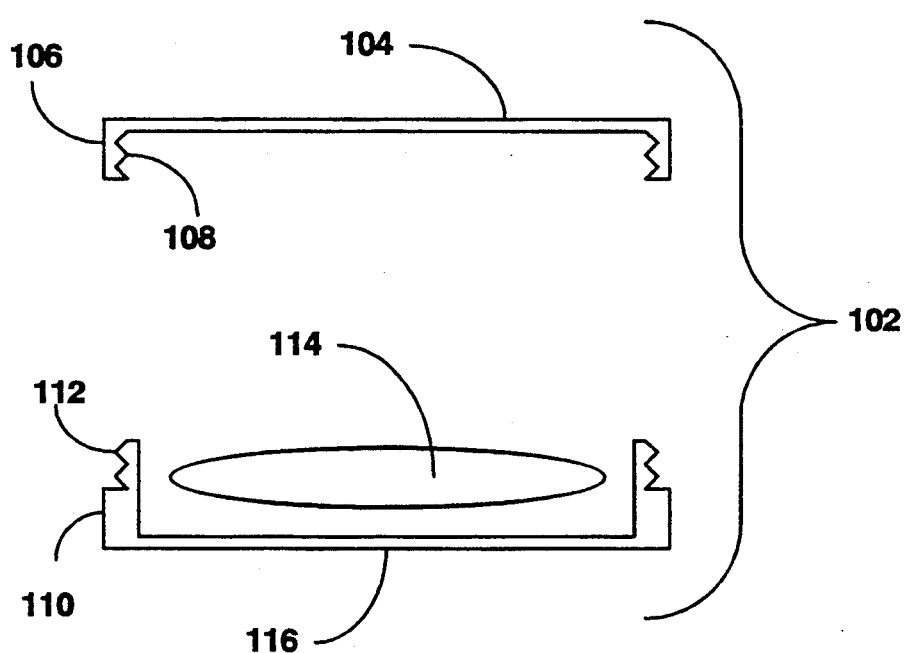
FIG. 2 shows a cross-sectional edge view of the token shown in FIG. 1.

Regarding FIG. 2, this figure shows a cross sectional end view of the token 102 as discussed above in relation to FIG. 1. The orientation of threads 108, 112 were reversed in this figure to indicate that threads 108, 112 can be arranged in any convenient manner. For ease of illustration, a single coin was discussed as raw material for token 102. Those skilled in the art will recognize that two coins may be used as raw material to increase the size of the first and second edges 106, 110, thereby increasing the available storage volume of token 102 when closed.

Figure 3:
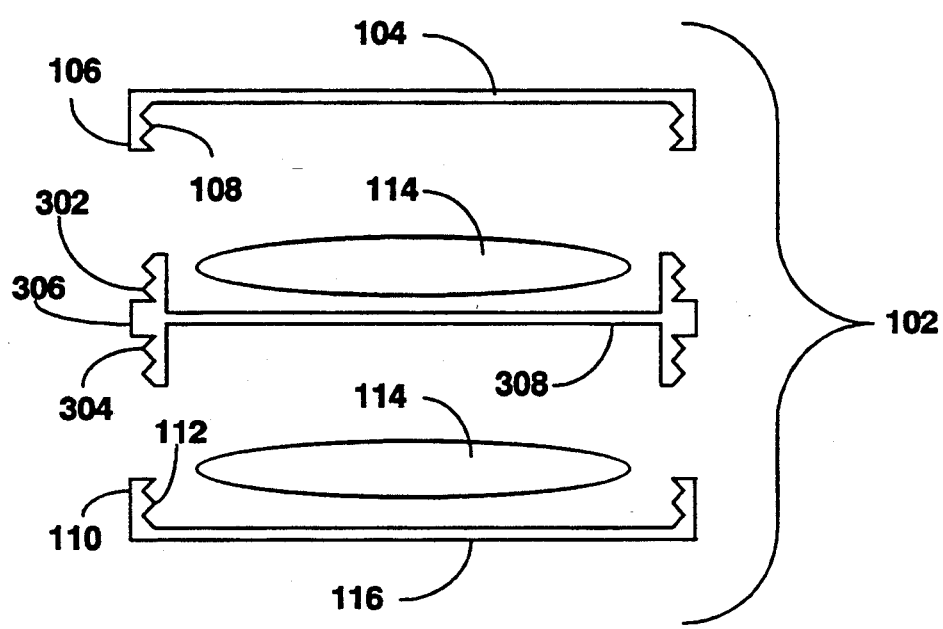
FIG. 3 shows an edge view of an alternative embodiment of the token shown in FIG. 1.

FIG. 3 shows an alternative embodiment of the invention. In this embodiment, the upper and lower portions of token 102 are spaced farther apart by the addition of an intermediate layer comprised of inner wall 308 which separates the internal space of token 102 into two compartments, each of which may hold an individual condom 114. Inner wall 308 is surrounded on its perimeter by third edge 306, third thread 302 and fourth thread 304. Threads 302, 304 allow the upper portion of token 102 and the lower portion of token 102 to be opened separately. Those skilled in the art will recognize that third edge 306 may be eliminated provided that token 102 has enough space remaining to hold both condoms 114.

Inner wall 308 may be eliminated entirely, leaving only the outer ring consisting of threads 302, 304 and third edge 306. In this configuration, threads 302, 304 and third edge 306 act as an intermediate ring spacer to increase the internal volume of token 102 and create a single larger storage area.

Figure 4:
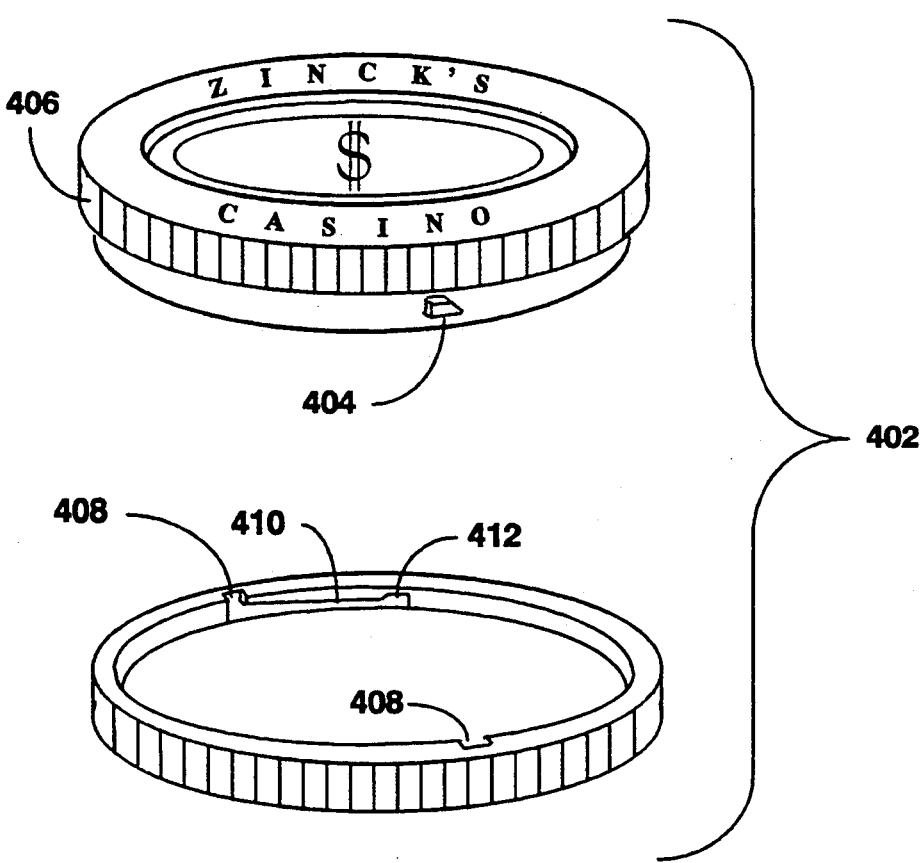
FIG. 4 shows an alternative embodiment of the token using a cam attachment mechanism.

FIG. 4 shows an alternative embodiment of the invention. Token 402 is molded such that when the upper and lower portions are joined, it passes for a souvenir casino chip. Those skilled in the art will recognize that the art work on the outside of token 402 can be altered to match any gaming chip for any casino, etc. Slots 408 are designed to accept cam followers 404 (The second cam follower 404 on the rear side of the upper portion of token 402 is not shown). After entering slots 408, the upper and lower portions of token 402 are rotated in opposite directions, forcing cam followers 404 down camming ramps 410 until cam followers 404 reach holding notches 412. At that point, the upper and lower sides of token 402 are locked in place.

Token 402 is made of flexible material to allow token 402 to open by rotating the upper and lower sides in the opposite directions from those used to close token 402. Because holding notches 412 and cam followers 404 have bevelled edges, as shown in the drawings, opposite rotation forces cam followers 404 to bend down to enable them to exit holding notches 412 and move along camming ramps 410 until cam followers 404 reach slots 408. Optional knurled edges are provided to assist rotation of the upper and lower portions of token 402. Those skilled in the art will recognize that a variety of camming techniques are well known in the art and can be used to accomplish closure of token 402. The particular camming technique disclosed herein is for illustrative purposes only.

Figure 5:
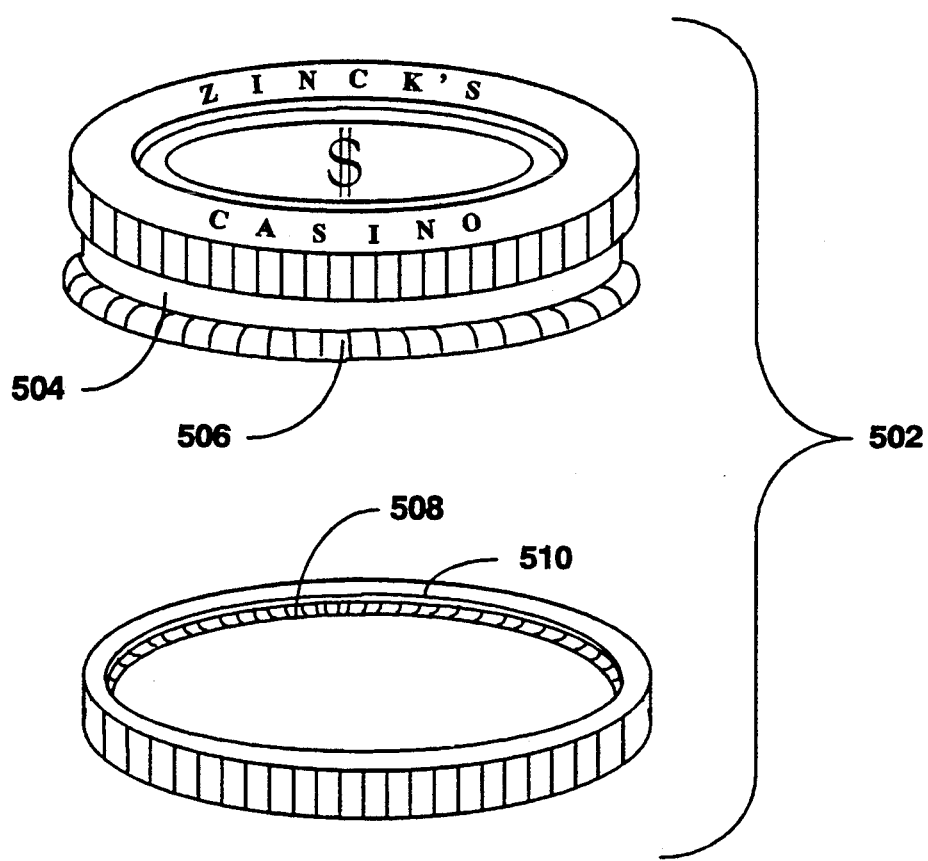
FIG. 5 shows another alternative embodiment of the token using a flexible attachment mechanism.

FIG. 5 shows an additional embodiment of the invention. Token 504 differs from token 402 in that the cam locking mechanism disclosed in FIG. 4 is replaced by a peelable mechanism. When token 502 is closed, inner wall 510 rests against outer wall 504. Peelable attachment 506 rests against peelable receptor 508. In this embodiment, some portion of token 502 must be flexible. Either the bottom portion of token 502 must be sufficiently flexible such that inner wall 510 may be stretched over rigid peelable attachment 506 or peelable attachment 506 must be sufficiently flexible such that peelable attachment 506 may be folded in to pass by inner wall 510. Of course, peelable attachment 506 and inner wall 510 may both be flexible.

Figure 6:
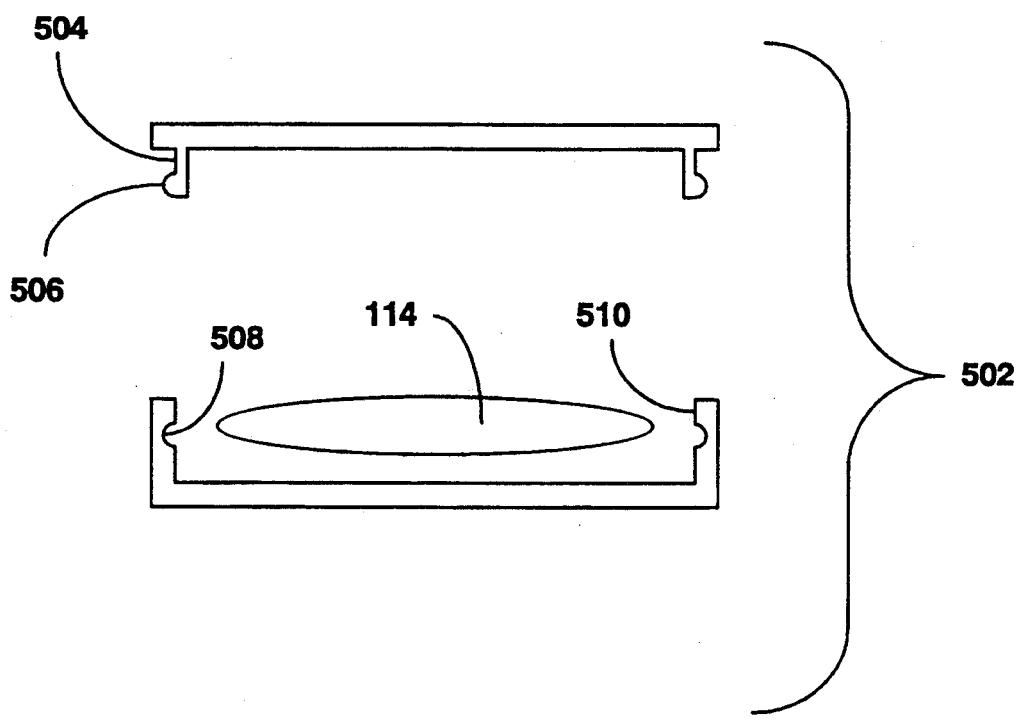
FIG. 6 shows a cross-sectional edge view of the token shown in FIG. 5.

FIG. 6 shows a cross sectional end view of token 502 as discussed above in regard to FIG. 5.

Figure 7:
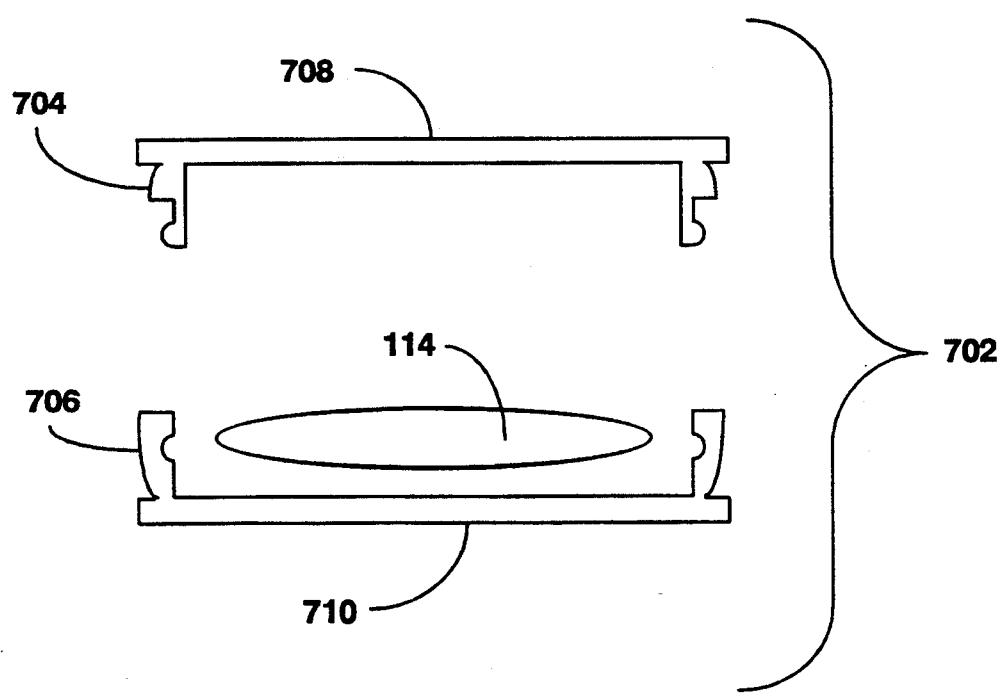
FIG. 7 shows a cross-sectional edge view of an alternative embodiment of the token shown in FIG. 5.
Figure 8:
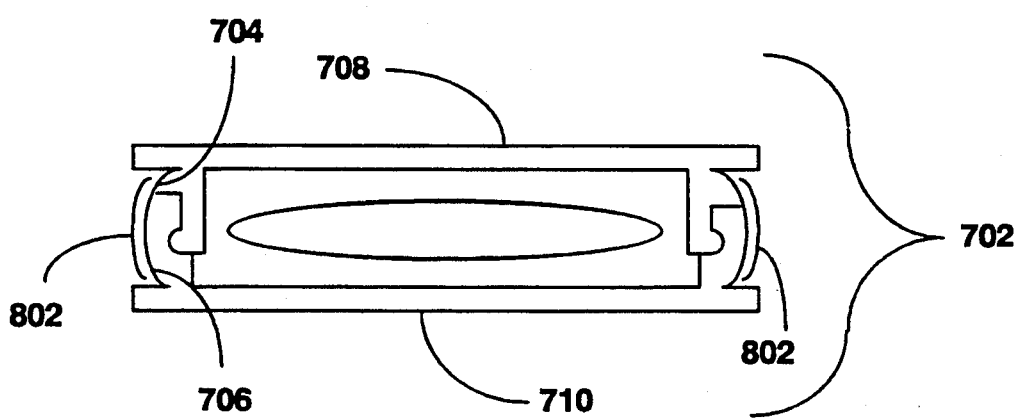
FIG. 8 shows the seal used in the cross-sectional edge view of an alternative embodiment of the token shown in FIG. 7.

FIGS. 7 and 8 show an alternative embodiment of the device shown in FIGS. 5 and 6. In this embodiment, first edge 704 and second edge 706 are inset from the edge of first side 708 and second side 710. FIG. 7 shows token 702 in open mode. FIG. 8 shows token 702 in closed mode. As can be seen in FIG. 8, by insetting first edge 704 and second edge 706, seal 802 can seal the perimeter of token 702 while being protected by the outer perimeter of first side 708 and second side 710. For purposes of illustration, first edge 704 and second edge 706 are shown having a high degree of curvature. Those skilled in the art will recognize that a shrink wrap seal will be self immobilizing in this configuration. However, first edge 704 and second edge 706 can also be substantially flat which will allow a properly colored seal 802 (or a clear seal) to appear to be part of token 702.

Figure 9:
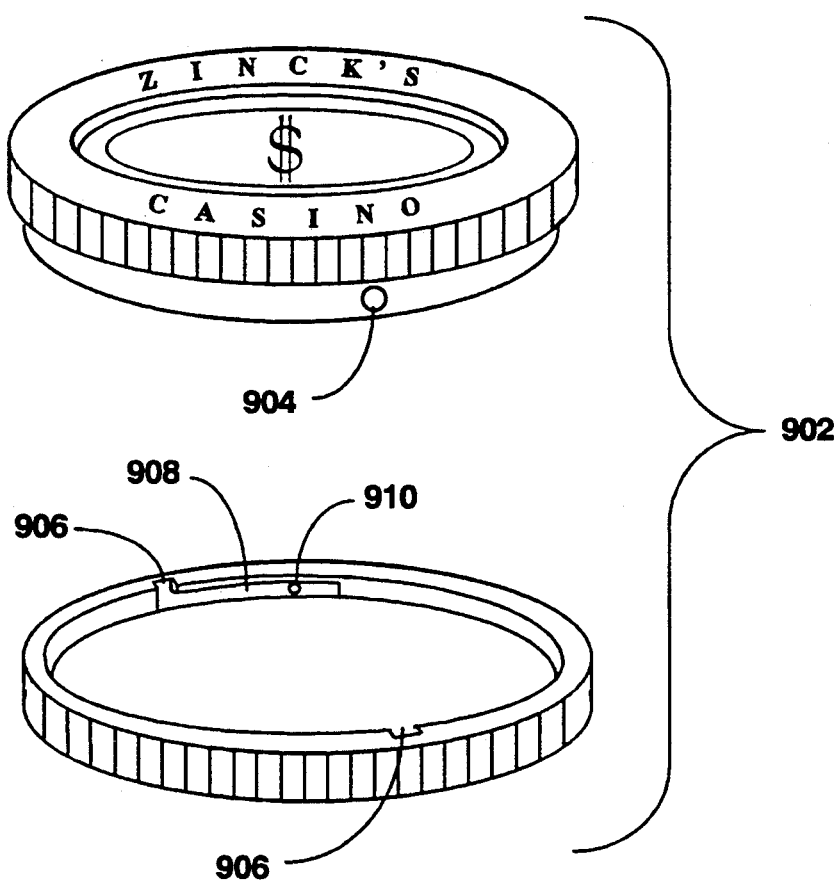
FIG. 9 shows another alternative embodiment of the token using a bead attachment mechanism.

FIG. 9 shows an embodiment similar to that shown in FIG. 4. However, in this embodiment, cam followers 404 are replaced by rounded beads 904. Rounded beads 904 are inserted into slots 906. The upper and lower portions of token 902 are then rotated in opposite directions, allowing rounded beads 904 to follow track 908 until rounded beads 904 come to rest within bead receptors 910. Those skilled in the art will recognize that the locations of rounded beads 904 and bead receptors 910 may be reversed. Likewise, rounded beads 904 may be a hard material such as a steel ball bearing or flexible material such as plastic. Bead locking devices are well known in the art. The bead lock shown in the preferred embodiment is for illustrative purposes only. Those skilled in the art will recognize that any suitable bead locking device may be used.

Figure 10:
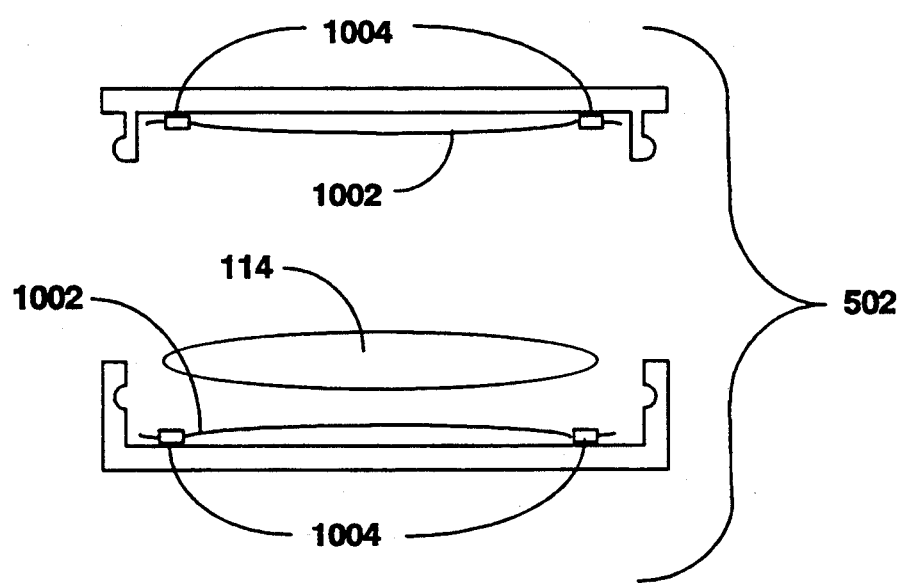
FIG. 10 shows a cross-sectional edge view of the token shown in FIG. 6 with removable condom attachment.

FIG. 10 shows an alternate embodiment in which a spring 1002 is used to push the condom 114 away from the upper and lower portions of token 502 when token 502 is opened. The spring 1002 is held in place by retainers 1004. One, or optionally (as shown), two springs 1002 may be used. The springs 1002 allow the condom 114 to be quickly and easily removed from token 502. Those skilled in the art will recognize that springs 1002 may be used with any of the embodiments disclosed herein.

Figure 11:
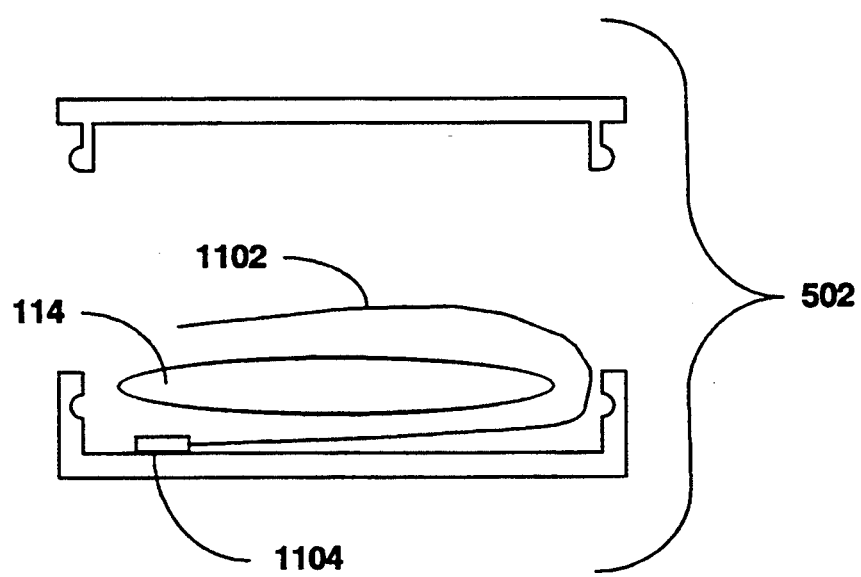
FIG. 11 shows an embodiment of the token shown in FIG. 10 with an alternative removable condom attachment.

In FIG. 11, an alternate method of removing condom 114 is shown. In this embodiment, tab retainer 1104 holds one end of tab 1102. The other end of tab 1102 is pulled upward manually or may be attached (not shown) to the other portion of token 502 and be pulled upward automatically when token 502 is opened.

Figure 12:
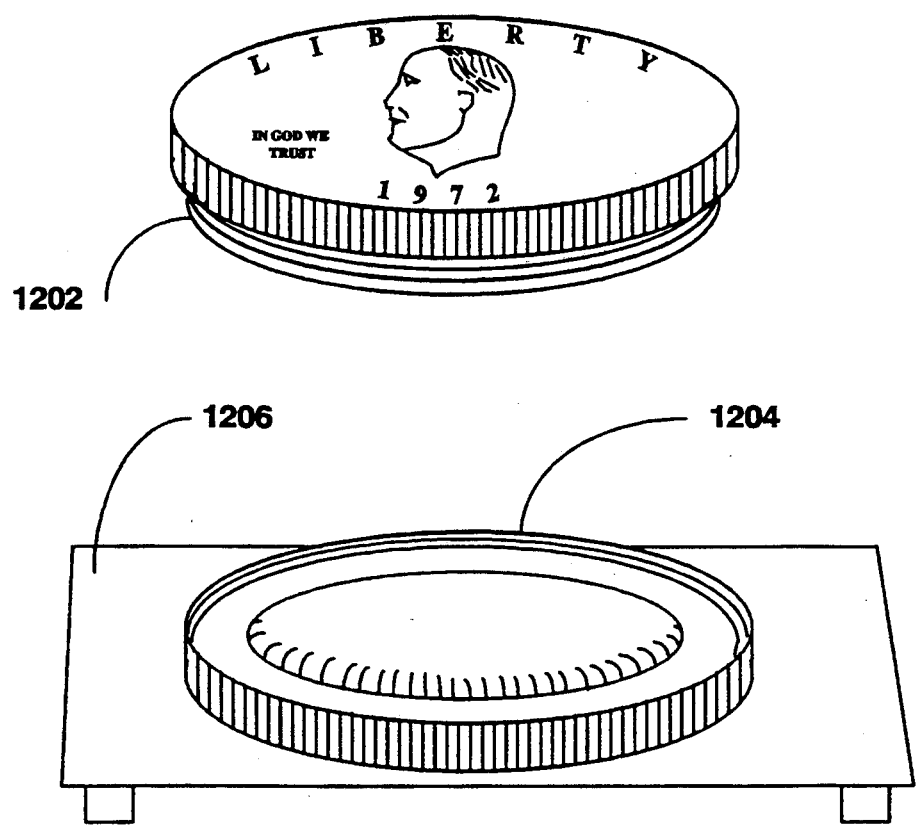
FIG. 12 shows an alternative embodiment of the token shown in FIG. 1.

FIG. 12 shows an alternative embodiment of the token disclosed in FIG. 1. In this embodiment, lower portion 1204 is attached to belt buckle 1206. Upper portion 1202 is removably attached to lower portion 1204. By attaching token 1202, 1204 to belt buckle 1206, the condom holder is disguised as a decorative article of apparel.

Figure 13:
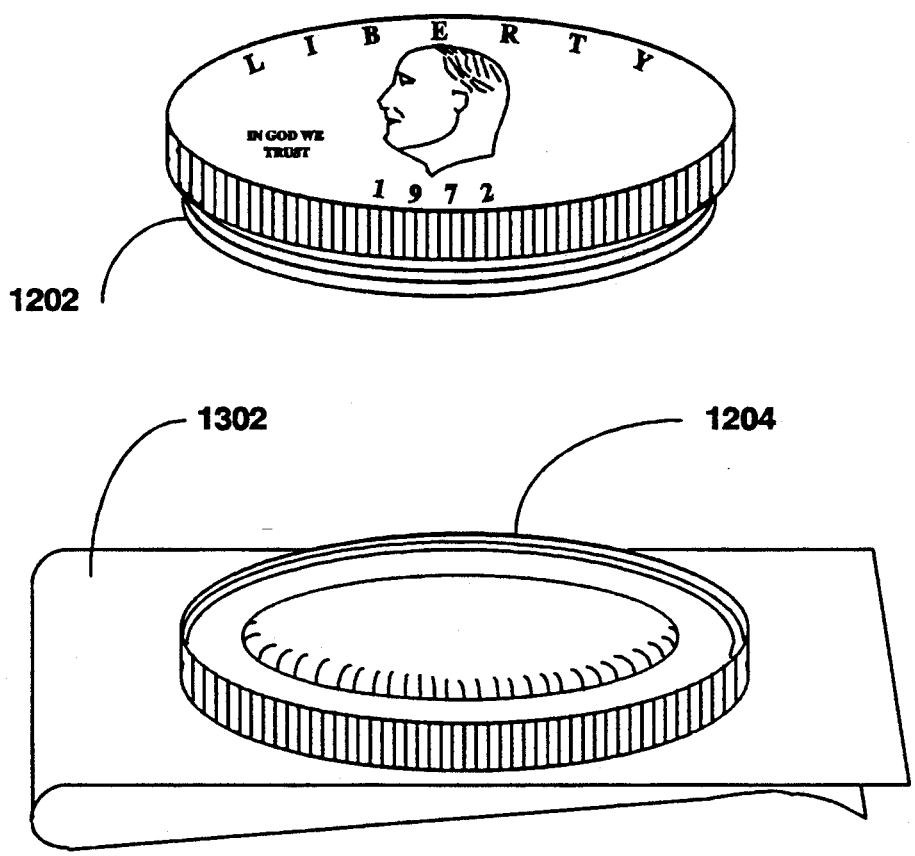
FIG. 13 shows another alternative embodiment of the token in FIG. 1.

FIG. 13 shows an alternative embodiment of the token disclosed in FIG. 1. In this embodiment, lower portion 1204 is attached to money clip 1302. Upper portion 1202 is removably attached to lower portion 1204. By attaching token 1202, 1204 to money clip 1302, the condom holder is disguised as a decorative accessory.

As can be seen from the foregoing, the invention disclosed herein allows condoms to be carried in camouflaged containers which permit user discretion and therefore encourage use. In particular, tokens that appear to be coins or souvenir casino chips can be left in a wallet or change purse indefinitely. They tend to be available since most people take wallets and purses with them most of the time, and they provide significant privacy since, even if seen, they are not perceived as condoms.

The embodiments disclosed herein provide a combination of benefits not heretofore found in the prior art. In particular, resistance to impact and environmental damage, ease of use, and camouflage to conceal the actual purpose of the device, thereby encouraging use. While the invention has been described with respect to a preferred embodiment thereof, it will be understood by those skilled in the art that various changes in detail my be made therein without departing from the spirit, scope, and teaching of the invention. For example, construction materials may vary to suit the particular embodiment, the token in the form of a coin or medal may be incorporated into jewelry, etc. Accordingly, the invention herein disclosed is to be limited only as specified in the following claims.

We claim:

1. A camouflaged token for concealment of a condom, comprising:
   a condom;
   a first side having a first integral edge means for removable attachment, the first edge means substantially encircling the perimeter of the first side;
   a second side having a second edge means substantially encircling the perimeter of the second side for removable attachment to the first edge means;
   removal means further comprising a spring device attached to the first side to push the condom away from the inner surface of the token when the token is opened;
   the first and second sides of a sufficient thickness to prevent impact damage to the condom during ordinary use, the first and second sides externally camouflaged such that the token appears to be a solid object and conceals the inner chamber when in the closed position; and
   the first edge means and the second edge means projecting substantially upward from the surface of the first side and the second side respectively such that when the first edge means and second edge means are attached to one another the first side and the second side are spaced apart from one another forming a storage area for the condom.

2. A camouflaged token, as in claim 1, wherein the removal means has a spring device on the second side to push the condom from the inner surface of the token when the token is opened.

3. A camouflaged token for concealment of a condom, comprising:
   a condom;
   a first side having a first integral edge means for removable attachment, the first edge means substantially encircling the perimeter of the first side;
   a second side having a second edge means substantially encircling the perimeter of the second side for removable attachment to the first edge means;

removal means further comprising a flexible tab attached to the first side, the first end of the flexible tab attached to the inner surface of the token and a second end of the flexible tab extending over the edge of the condom such that when the token is opened and the second end of the flexible tab is pulled, the condom is lifted from the inner surface of the token;

the first and second sides of a sufficient thickness to prevent impact damage to the condom during ordinary use, the first and second sides externally camouflaged such that the token appears to be a solid object and conceals the inner chamber when in the closed position; and the first edge means and the second edge means projecting substantially upward from the surface of the first side and the second side respectively such that when the first edge means and second edge means are attached to one another the first side and the second side are spaced apart from one another forming a storage area for the condom.

4. A camouflaged token, as in claim 3, wherein the second end of the tab is attached to the inner surface of the second side such that when the token is opened, the tab automatically ejects the condom from the token.

* * * * *